United States Patent [19]

Tamura

[11] Patent Number: 5,044,494

[45] Date of Patent: Sep. 3, 1991

[54] PACKAGING MEANS FOR A PLURALITY OF PAIRS OF THROWAWAY THREE-DIMENSIONAL HAND COVERINGS

[75] Inventor: Shinpei Tamura, Hiroshima, Japan

[73] Assignee: Nippon Technics Kabushiki Kaisha, Hiroshima, Japan

[21] Appl. No.: 355,178

[22] Filed: May 19, 1989

[30] Foreign Application Priority Data

May 28, 1988 [JP] Japan .................................. 63-131074

[51] Int. Cl.⁵ .......................................... B65D 85/18
[52] U.S. Cl. ..................... 206/299; 206/438
[58] Field of Search ............................. 383/37, 38, 39; 206/278, 438, 602, 494, 554, 299, 820; 229/87 A

[56] References Cited

U.S. PATENT DOCUMENTS

| 1,046,337 | 12/1912 | Schoettle | 229/162 X |
| 1,842,728 | 1/1932 | Molins | 206/254 |
| 2,754,867 | 7/1956 | Langer | 383/39 |
| 2,810,417 | 10/1957 | Yerk | 206/278 |
| 3,181,695 | 5/1965 | Taterka et al. | 206/299 |
| 3,187,987 | 6/1965 | Langdon | 206/299 X |
| 3,486,657 | 12/1969 | Blatz | 206/299 X |
| 3,746,152 | 7/1973 | Allen | 206/299 |
| 4,294,353 | 10/1981 | Focke et al. | 206/602 |
| 4,515,270 | 5/1985 | Alvarabo | 206/438 |

FOREIGN PATENT DOCUMENTS 2914590 10/1980 Fed. Rep. of Germany ...... 206/494

Primary Examiner—Paul T. Sewell
Assistant Examiner—Jacob K. Ackun, Jr.
Attorney, Agent, or Firm—Flynn, Thiel, Boutell & Tanis

[57] ABSTRACT

A packaging case comprising two boxes or bags can be open right and left or closed like a book. At the time when the packaging case is open, holes or slits provided at the upper surfaces of the boxes or bags are appeared so that a pair of three-dimensional hand coverings stored in the boxes or bags can be taken out one by one. At the time when the packaging case is closed, the holes or the slits are concealed to prevent the boxes or the bags from entering of the dust.

1 Claim, 2 Drawing Sheets

5,044,494

PACKAGING MEANS FOR A PLURALITY OF PAIRS OF THROWAWAY THREE-DIMENSIONAL HAND COVERINGS

BACKGROUND OF THE INVENTION

1. Field of the Invention

It is preferable that doctors or dentists contacting the patients of AIDS or other disease wear the three-dimensional hand coverings made of high polymer material to prevent a direct infection from the patients. The three-dimensional hand coverings made of high polymer material are preferably thrown away or discarded to prevent infecting other patients with bacilli attached to the three-dimensional hand coverings. In the case where the throwaway three-dimensional hand coverings are employed, it is preferable that the three-dimensional hand coverings are made of a synthetic resin sheet for manufacturing the three-dimensional hand coverings with low cost. The three-dimensional hand coverings made of the synthetic resin sheet are required to be bisymmetrical for fitting to the hands.

It is an object of the present invention to provide a package means for storing therein and taking out therefrom a plurality of pairs of the throwaway three-dimensional hand coverings which are bisymmetrical.

2. Description of the Prior Art

The throwaway three-dimensional hand coverings made of the soft synthetic resin sheet used conventionally by eye doctors, etc. comprises two sheets which are stacked one on another and welded in conformity with shapes of both hands, and cut off along the welded shape. The three-dimensional hand coverings are usable in both hands and stored in a single case which case does not differentiate the three-dimensional right hand covering from the three-dimensional left hand covering. It is disadvantageous if the three-dimensional hand coverings are to be worn by both hands, because they do not properly fit both hands. To solve this problem, there is proposed the throwaway three-dimensional hand coverings made of a soft synthetic resin sheet which are fit to both hands as disclosed in Japanese Laid-Open Publication No. 63-219605.

SUMMARY OF THE INVENTION

It is an object of the present invention to provide a packaging means for a plurality of pairs of throwaway three-dimensional hand coverings made of soft synthetic resin capable of distinguishing the three-dimensional right hand covering from the three-dimensional left hand covering and enabling the three-dimensional right and left hand coverings to be fit to the right and left hands with ease.

To achieve the above object, the present invention has the construction as set forth hereinafter.

A packaging means in box shape for housing a plurality of pairs of three-dimensional right and left hand coverings comprises, as shown in FIGS. 1 and 2, a left side box 2a of a rectangular parallelepiped shape for packaging the three-dimensional left hand coverings stacked one on another and having an upper surface 3a provided with a hole 5a for taking out the three-dimensional left hand coverings therefrom and a ridge 4a extended longitudinally in full length of one end edge of the upper surface 3a, a right side box 2b of a rectangular parallelepiped shape for packaging the three-dimensional right hand coverings stacked one on another and having an upper surface 3b provided with a hole 5b for taking out the three-dimensional right hand coverings therefrom and a ridge 4b extended longitudinally in full length of one end edge of the upper surface 3b. The left and right boxes 2a, 2b are foldably connected with each other via the ridges 4a, 4b. In the case where the three-dimensional hand coverings are shipped, transferred, stored, the upper sufaces 3a, 3b of both boxes 2a, 2b are another to overlap the both boxes 2a, 2b to form the rectangular parallelepiped shape 6 which has a height twice the height of one box, but occupies a small space while in the case where it is used, the left and right boxes 2a, 2b are unfolded and arranged in left and right, as shown in FIG. 2, the three-dimensional left and right hand coverings 1a, 1b stacked one over the other and stored in the left and right boxes 2a, 2b are sequentially taken out one by one through the holes 5a, 5b.

A packaging means in bag shape for storing a plurality of pairs of three-dimensional right and left hand coverings comprises, as shown in FIGS. 3 and 4, a left bag 12a of a rectangular shape for packaging the three-dimensional left hand coverings 1a stacked one on another and having an upper surface 13a provided with a slit 15a for taking out the three-dimensional left hand coverings therefrom, a right bag 12b of a rectangular shape for packaging the three-dimensional right hand coverings 12b stacked one on another and having an upper surface 13b provided with a slit 15b for taking out the three-dimensional right hand coverings therefrom in which the left and right bags 12a, 12b are foldably connected with each other via a partition welding portion 18. The packaging bag has a plurality of the three-dimensional left hand coverings 1a stored in the left bag 12a and a plurality of three-dimensional right hand coverings stored in the right bag 12b. In the case where the three-dimensional hand coverings are shipped, transferred, stored, the upper sufaces 13a, 13b of both bags 12a, 12b are pressed together to overlap the both bags 12a, 12b to form one double folded bag 16 which has a height twice the height of one box, but occupies a small space, while in the case where it is used, the left and right bags 12a, 12b are unfolded and arranged in left and right, as shown in FIG. 4, the three-dimensional left and right hand coverings 1a, 1b stacked one over the other and stored in the left and right bags are sequentially taken out one by one through the slits 15a, 15b.

The above and other objects, features and advantages of the present invention will become more apparent from the following description taken in conjucntion with the accompanying drawings.

DESCRIPTION OF THE PREFERRED EMBODIMENT

Figure 1:
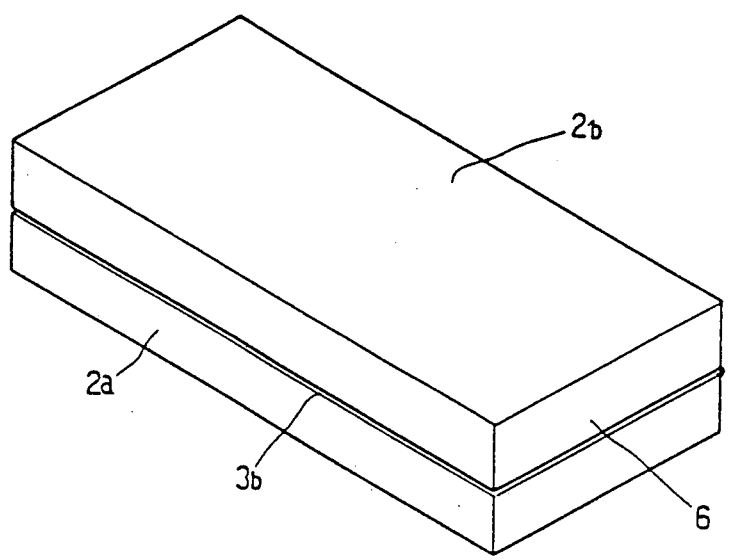
FIG. 1 is a perspective view of assistance in explaining a folding state of a packaging case for a pair of throwaway three-dimensional hand coverings according to a first embodiment of the present invention.
Figure 2:
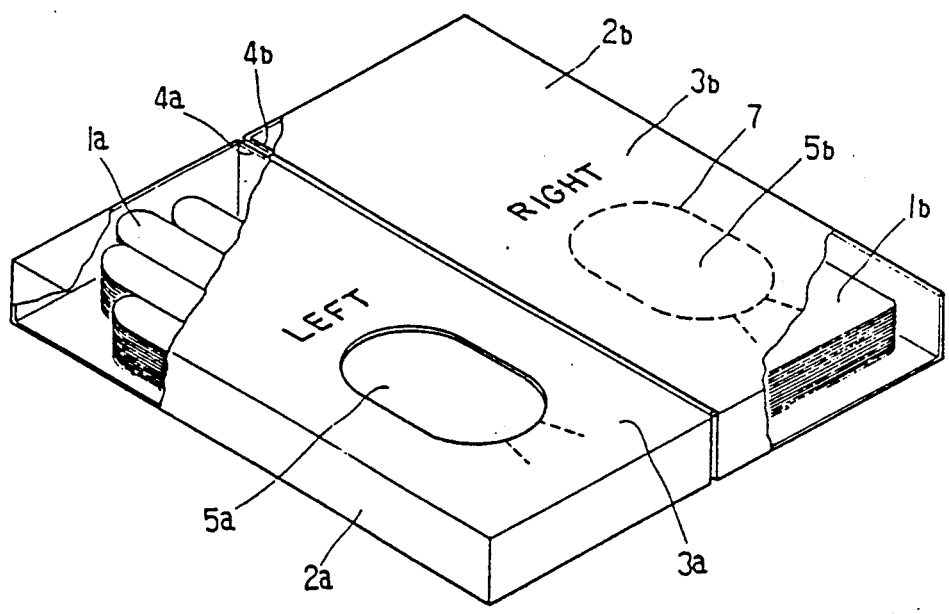
FIG. 2 is a perspective view of assistance in explaining an unfolding state of a packaging case for a pair of throwaway three-dimensional hand coverings according to the first embodiment of the present invention.

First Embodiment (FIGS. 1 and 2)

A first embodiment of a packaging means for a plurality of pairs of throwaway three-dimensional hand coverings will be described with reference to FIGS. 1 and 2.

A packaging means in box shape for storing a plurality of pairs of three-dimensional left and right hand coverings comprises a left box 2a of a rectangular parallelepiped shape for packaging the three-dimensional left hand coverings stacked one on another and having an upper surface 3a provided with a hole 5a for taking out the three-dimensional left hand coverings therefrom and a ridge 4a extended longitudinally in full length of one end edge of the upper surface 3a, a right box 2b made of the same material as that of the left box 2a and having the same shape as that of the left box 2a for packaging the three-dimensional right hand coverings stacked one on another and having an upper surface 3b provided with a hole 5b for taking out the three-dimensional right hand coverings therefrom and a ridge 4b extended longitudinally in full length of both one end edges of the upper surface 3b. The left and right boxes 2a, 2b are foldably connected with each other via ridges 4a, 4b extended longitudinally in full length of one end edge of the both boxes. As shown in FIG. 1, it is possible that the upper sufaces 3a, 3b of both boxes 2a, 2b are brought into mutual contact to overlap the both boxes 2a, 2b to form the rectangular parallelepipedon 6 which has a height twice the height of one box, or as shown in FIG. 2, the left and right boxes 2a, 2b are unfolded and arranged in left and right. On the upper surfaces of the left and right boxes 2a, 2b, there is specified characters (for example, the characters LEFT and RIGHT) or figures showing that the three-dimensional left and right hand coverings are stored in the left and right boxes. The holes 5a, 5b for taking out the three-dimensional hand coverings are not necessarily to be open when the three-dimensional hand coverings are shipped, but have slits 7 to be open with ease. In the case where the three-dimensional hand coverings are shipped, transferred, stored, the upper sufaces 3a, 3b of both boxes 2a, 2b are brought together to overlap the both boxes 2a, 2b to form the rectangular parallelepipedon 6 which has a height twice the height of one box, but occupies a small space. In the case where the three-dimensional hand coverings are used, the left and right boxes 2a, 2b are unfolded and arranged in left and right as shown in FIG. 2 so that the three-dimensional left and right hand coverings 1a, 1b lied one over the other and stored in the left and right boxes 2a, 2b are taken out one by one through holes 5a, 5b.

Figure 3:
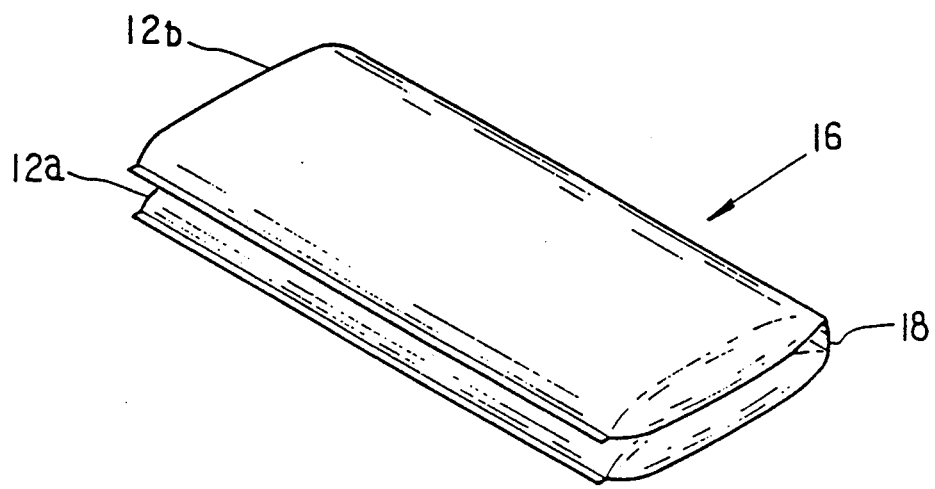
FIG. 3 is a perspective view of assistance in explaining a folding state of a packaging bag for a pair of throwaway gloves according to a second embodiment of the present invention.
Figure 4:
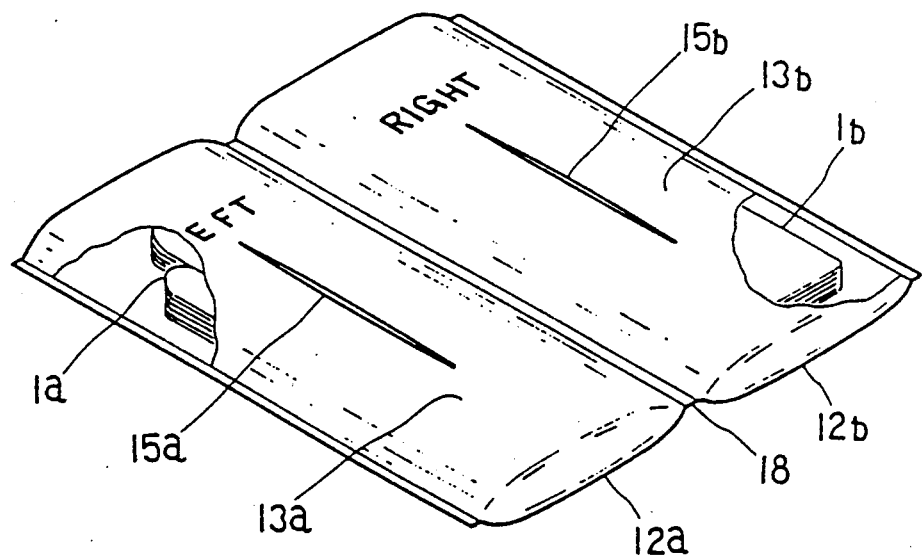
FIG. 4 is a perspective view of assistance in explaining an unfolding state of a packaging bag for a pair of throwaway three-dimensional hand coverings according to the second embodiment of the present invention.

Second Embodiment (FIGS. 3 and 4)

A second embodiment of a packaging means for a pair of throwaway three-dimensional hand coverings will be described with reference to FIGS. 3 and 4.

A packaging means in bag shape for storing a plurality of pairs of three-dimensional left and right hand coverings comprises a left bag 12a of a rectangular shape for packaging the three-dimensional left hand coverings 1a stacked one on another and having an upper surface 13a provided with a slit 15a for taking out the three-dimensional left hand coverings therefrom, a right bag 12b made of the same material as that of the left bag 12a and having the same shape as that of the left bag 12a for packaging the three-dimensional right hand coverings stacked over the other stored in the right bag 12b and having an upper surface 13b provided with a slit 15b for taking out the three-dimensional right hand coverings therefrom. The left and right bags 12a, 12b are foldably connected with each other via a partition welding portion 18. As shown in FIG. 3, it is possible that the upper sufaces 13a, 13b of both bags 12a, 12b are brought together to overlap the both bags 12a, 12b to form the double folded bag 16 which has a height twice the height of one bag, or as shown in FIG. 4, the left and right bags 12a, 12b are unfolded and arranged in left and right. On the upper surfaces of the left and right bags 12a, 12b, there is specified characters or figures showing that the three-dimensional left and right hand coverings are stored in the left and right bags. The packaging bag has a plurality of the three-dimensional left hand coverings 1a stored in the left bag 12a and a plurality of three-dimensional right hand coverings stored in the right bag 12b. In the case where the three-dimensional hand coverings are shipped, transferred, stored, the upper sufaces 13a, 13b of both bags 12a, 12b are brought together to overlap the both bags 12a, 12b to form one double folded bag 16 which has a height twice the height of one bag, but occupies a small space. In the case where it is used, the left and right bags 12a, 12b are unfolded and arranged, as shown in FIG. 4, the three-dimensional left and right hand coverings 1a, 1b stacked one over the other and stored in the left and right bags are taken out one by one through the slits 15a, 15b.

With the arrangement of the packaging means for a pair of throwaway three-dimensional hand coverings as set forth above, the packaging means can be folded at the time of shipment, transfer, storage of the three-dimensional hand covering to reduce the space to be occupied with the simple shape and strucure. Especially, the packaging means is very convenient since each pair of three-dimensional hand coverings can be controlled or managed at the same time.

At the time of use of the three-dimensional hand covering, both boxes 2a, 2b or bags 12a, 12b are unfolded to take out in turn without fail the three-dimensional left and right hand coverings 1a, 1b stacked one over the other in the boxes 2a, 2b or bags 12a, 12b through the left and right holes 5a, 5b of the left and right boxes 2a, 2b or the left and right slits 15a, 15b of the left and right bags 12a, 12b. The packaging boxes or the bags do not occupy a large space when they are used. The packaging boxes or bags keep clean in case when they are folded.

Accordingly, the present packaging means are very convenient for packaging the throwaway three-dimensional hand coverings for use in medical or drug treating purpose.

Although the invention has been described in its preferred form with a certain degree of particularity, it is to be understood that many variations and changes are possible in the invention without departing from the scope thereof.

What is claimed is:

1. A packaging case for a plurality of pairs of throwaway three-dimensional hand coverings, comprising:
an opaque left box having a rectangular shape, said left box being filled with a plurality of three-dimensional left hand coverings which are stacked upon each other, said left box having a hole in an upper surface thereof for permitting removal of said left hand coverings therefrom, and said left box having a ridge which extends longitudinally along one edge thereof;

an opaque right box having a rectangular shape, said right box being filled with a plurality of three-dimensional right hand coverings which are stacked on each other, said right box having a hole in an upper surface thereof for permitting removal of said right hand coverings therefrom, and said right box having a ridge which extends longitudinally along one edge thereof;

said left and right boxes being foldably connected with each other along said ridges thereof;

said left and right hand coverings defining respective shapes which are different but are substantially mirror images of each other, said left and right boxes having visible indicia marked on said upper surfaces thereof for uniquely identifying each said box and facilitating selecting said left and right hand coverings; and each said hand covering including a base portion and a plurality of finger portions extending from said base portion, said hand coverings being stacked in said boxes such that said finger portions overlie each other and said base portions overlie each other, said holes in said upper surfaces of said boxes being dimensioned so as to overlie only said base portions of said hand coverings and being spaced from both longitudinal ends of the associated box, said finger portions being covered by said upper surfaces, said visible indicia overlying a part of said hand coverings between said hole and said finger portions, each said base portion having a palm side and a back side which faces oppositely away from said palm side, and said back sides of said base portions facing toward the associated holes and upper surfaces of said boxes.

* * * * *